(12) United States Patent  (10) Patent No.: US 6,589,197 B1
Doi et al.  (45) Date of Patent: Jul. 8, 2003

(54) FLUID PASSAGE CHANGE-OVER APPARATUS FOR MEDICAL TREATMENT

(75) Inventors: Hiroyuki Doi, Sapporo (JP); Kazuhiro Shinmoto, Iwakuni (JP); Zyunya Fujii, Hatsukaichi (JP); Seishin Tanaka, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 0 days.

(21) Appl. No.: 09/763,198

(22) PCT Filed: Oct. 9, 1998

(86) PCT No.: PCT/JP98/04557

§ 371 (c)(1),
(2), (4) Date: Feb. 20, 2001

(87) PCT Pub. No.: WO00/10626

PCT Pub. Date: Mar. 2, 2000

(30) Foreign Application Priority Data

Aug. 19, 1998 (JP) ............................................. 10-249226

(51) Int. Cl.⁷ ................................................ A61M 39/00
(52) U.S. Cl. ............................ 604/6.1; 604/29; 604/32; 604/34; 251/4; 137/862
(58) Field of Search ................................ 604/4.01, 5.01, 604/6.1, 29, 32, 33, 34, 80, 246, 247, 248, 258, 410; 251/4, 6, 9; 137/625.41, 861, 862, 872, 874

(56) References Cited

U.S. PATENT DOCUMENTS 3,411,534 A * 11/1968 Rose ........................... 137/595
4,821,996 A *  4/1989 Bellotti et al. .............. 251/230

FOREIGN PATENT DOCUMENTS

| JP | 59-50277 | 3/1984 |
| JP | 2-502882 | 9/1990 |
| JP | 8-727 | 1/1996 |

* cited by examiner

Primary Examiner—Gene Mancene
Assistant Examiner—Patrick Buechner
(74) Attorney, Agent, or Firm—Armstrong, Westerman & Hattori, LLP.

(57) ABSTRACT

A medical fluid passage switching apparatus comprising: at least, a rotatable shaft F; a cam C which is rotated in relation to the rotating movement of the shaft F to close and open divided tubes for determining a passage of a fluid; and a housing L having tube accepting holes I and so arranged to enable the holding of the cam C, is provided. More particularly, provided are such a medical fluid passage switching apparatus in a continuous ambulatory peritoneal dialysis (CAPD) system and a tube which is decreased in the diameter and/or thinned in the wall at a region where the cam or a combination of the cam and the clamp is engaged for closing and opening.

15 Claims, 13 Drawing Sheets

Fig.6
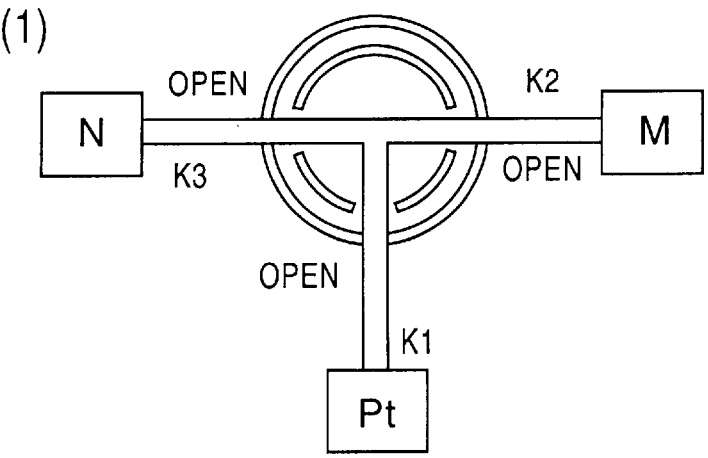
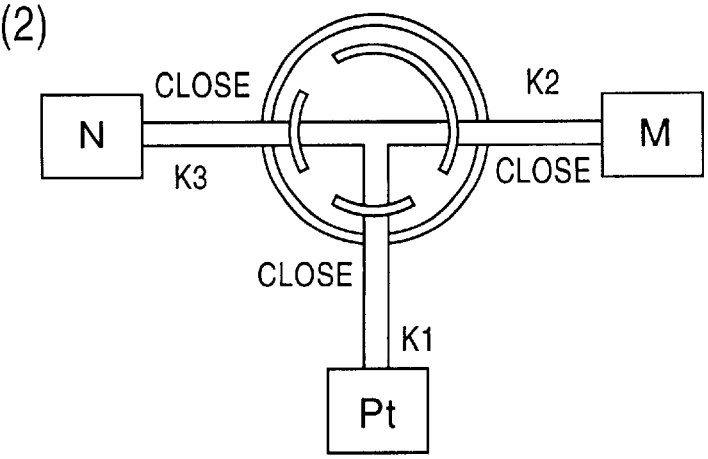
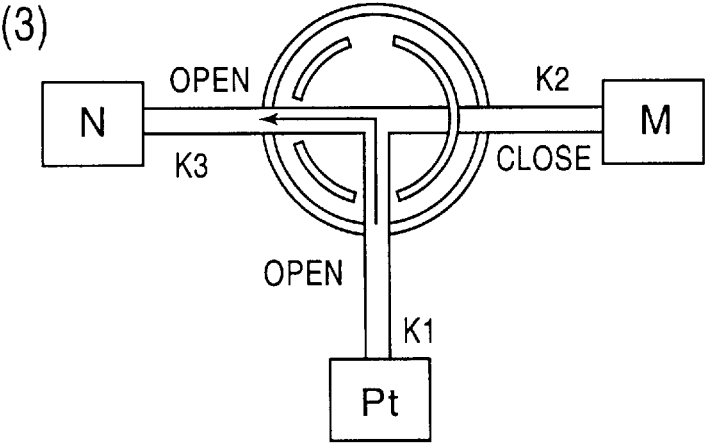

Fig.7
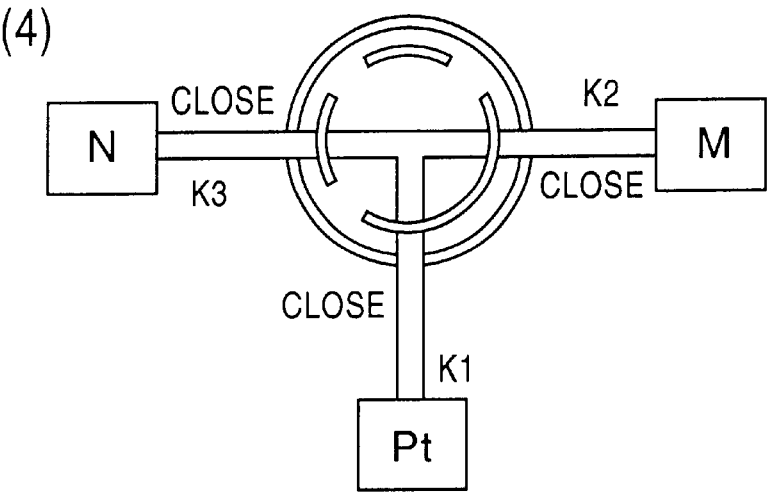
(4)
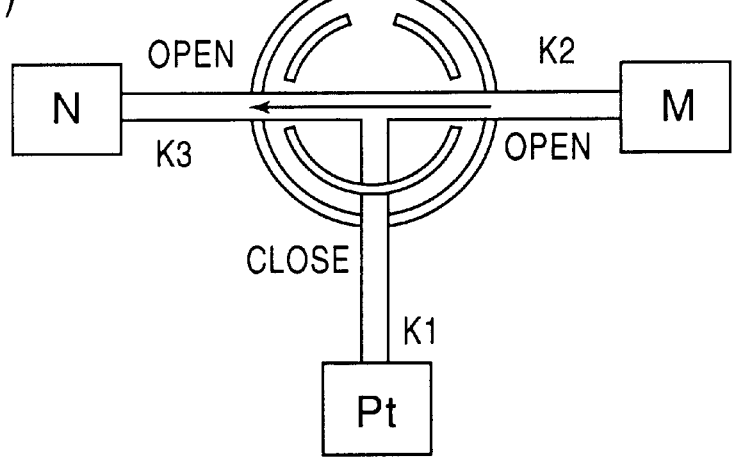
(5)
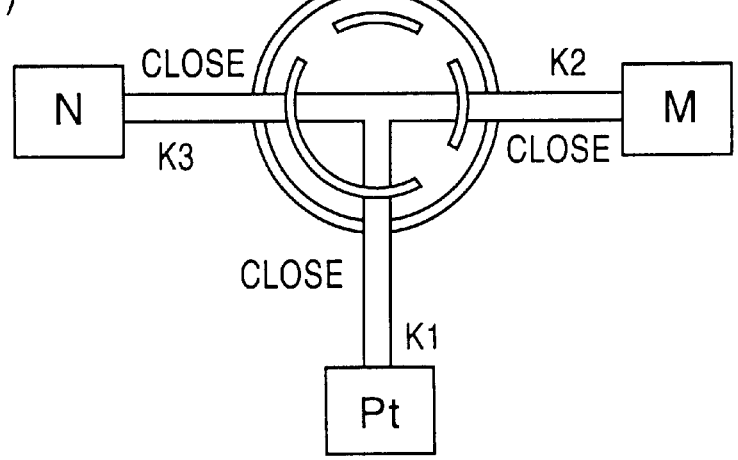
(6)

Fig.8
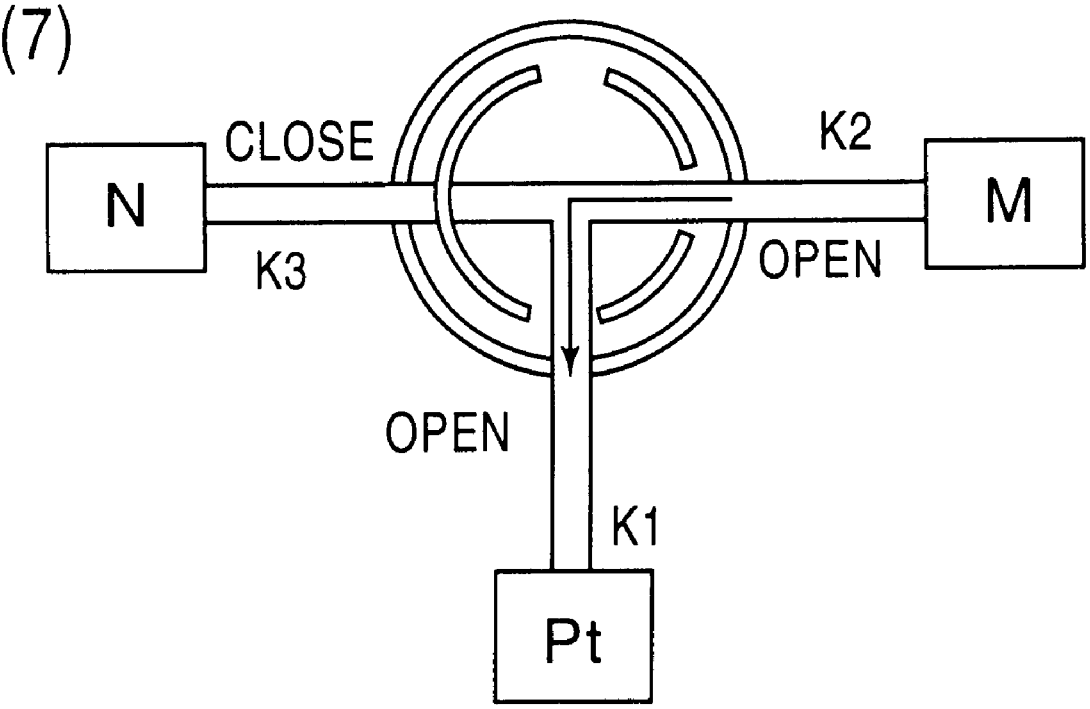
(7)
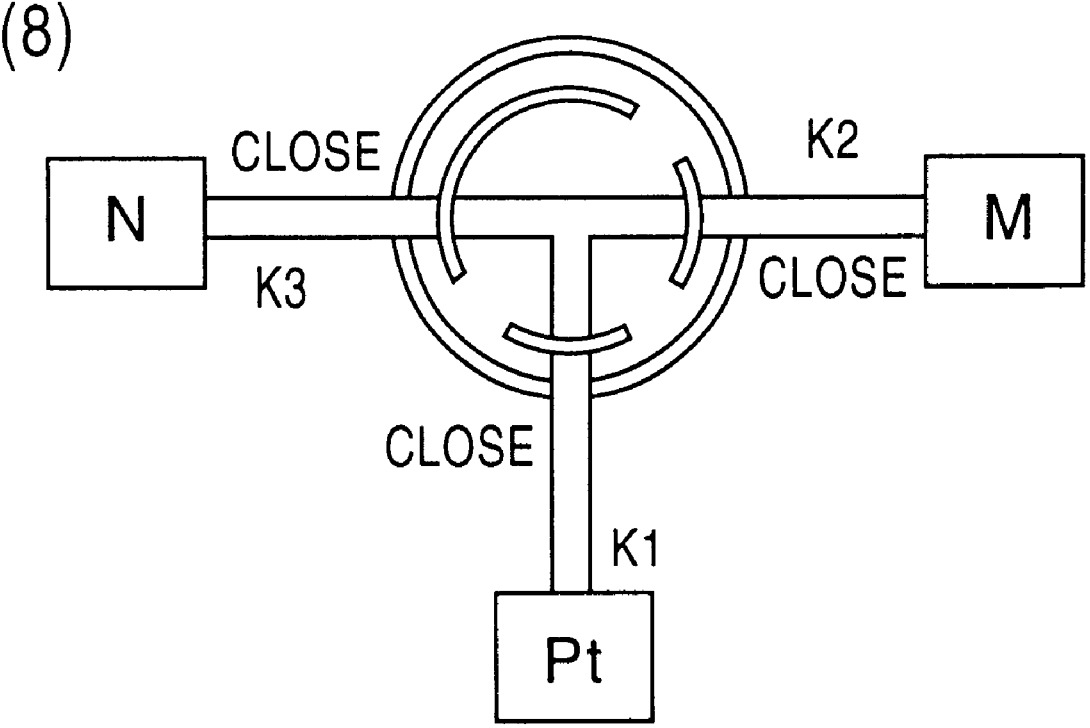
(8)

Fig.9
(1)
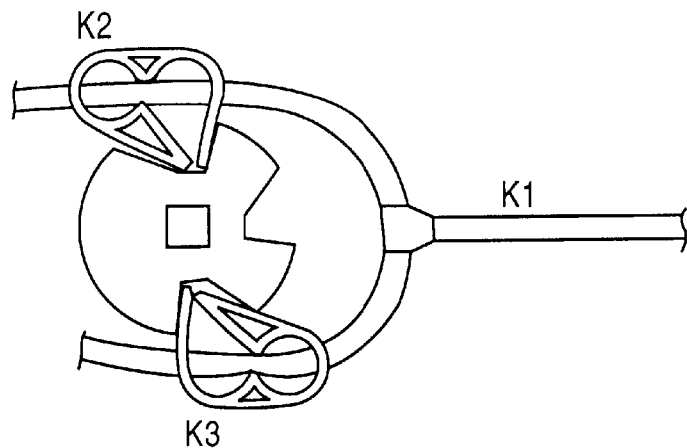
(2)
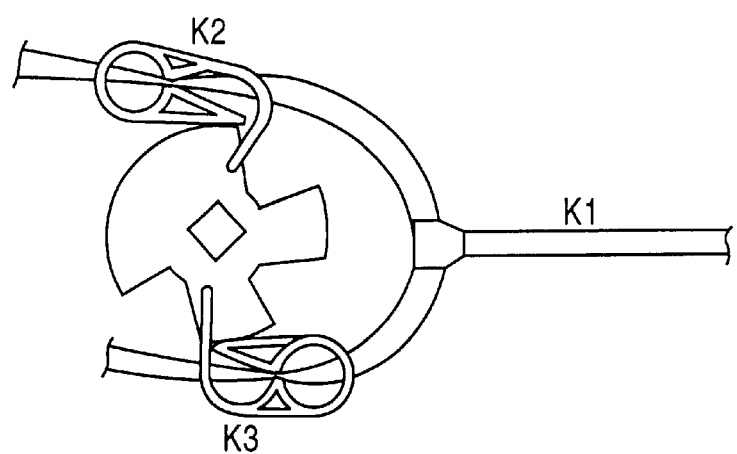
(3)
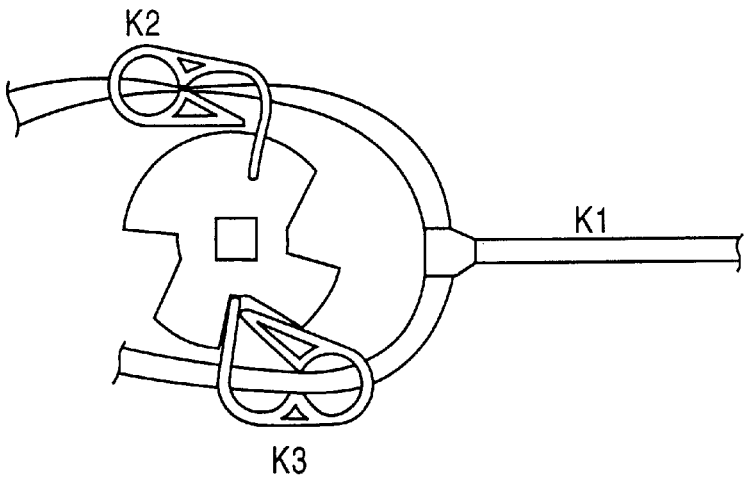

Fig.10
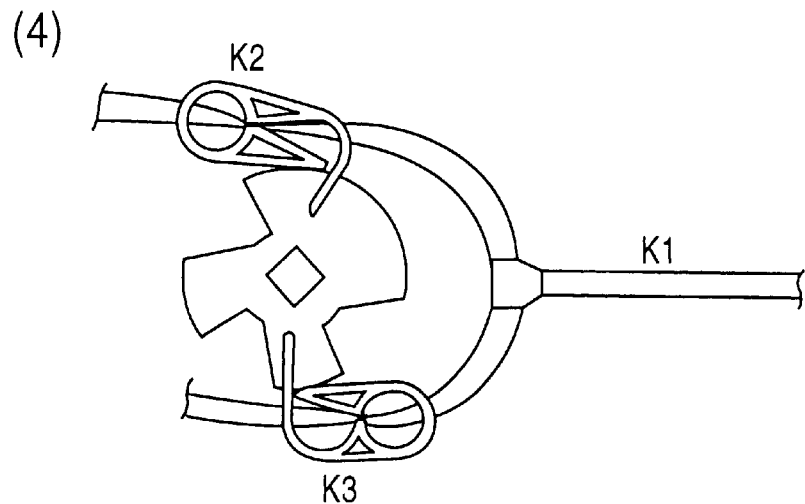
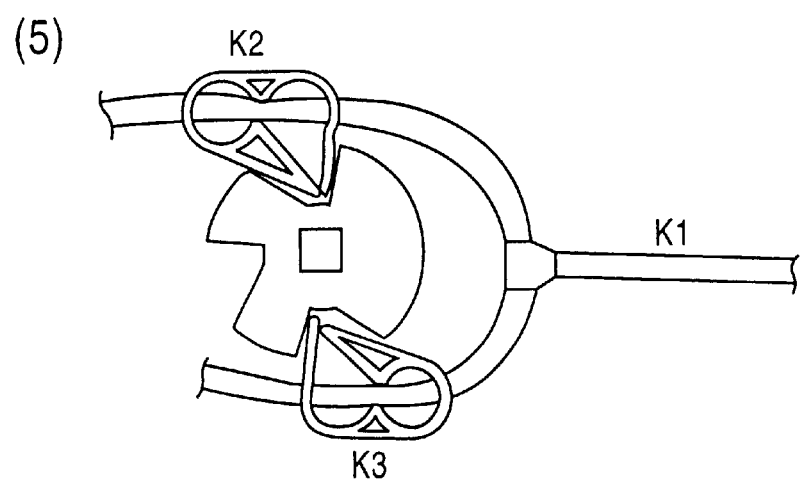
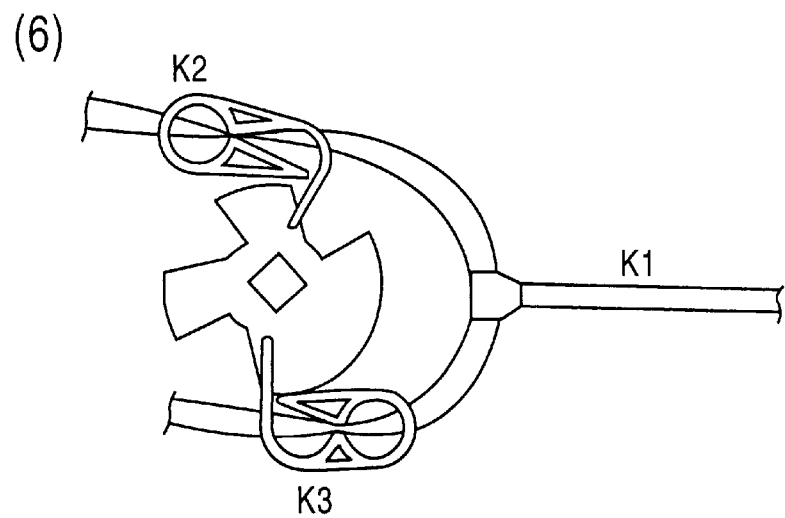

Fig.11
(7)
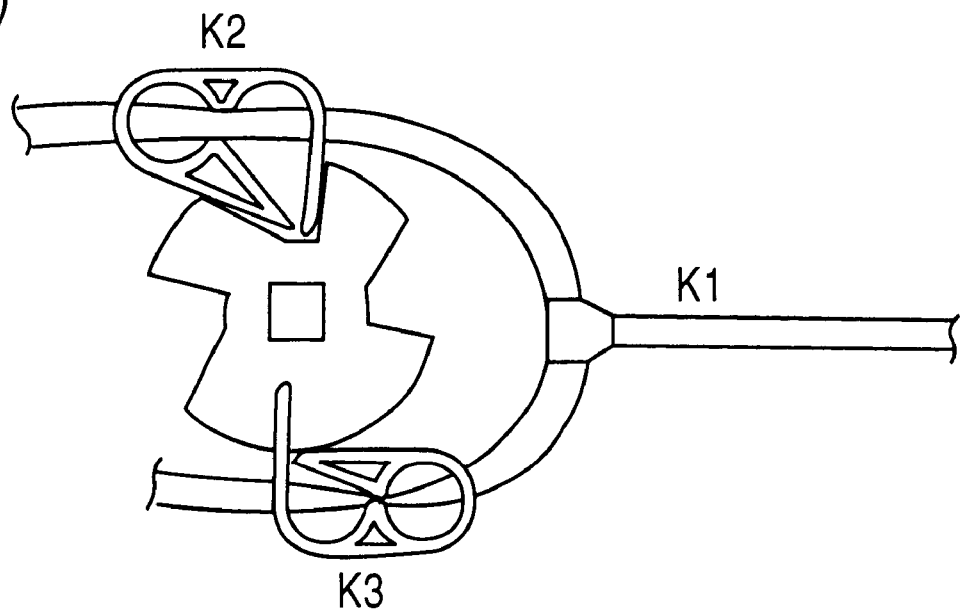
(8)
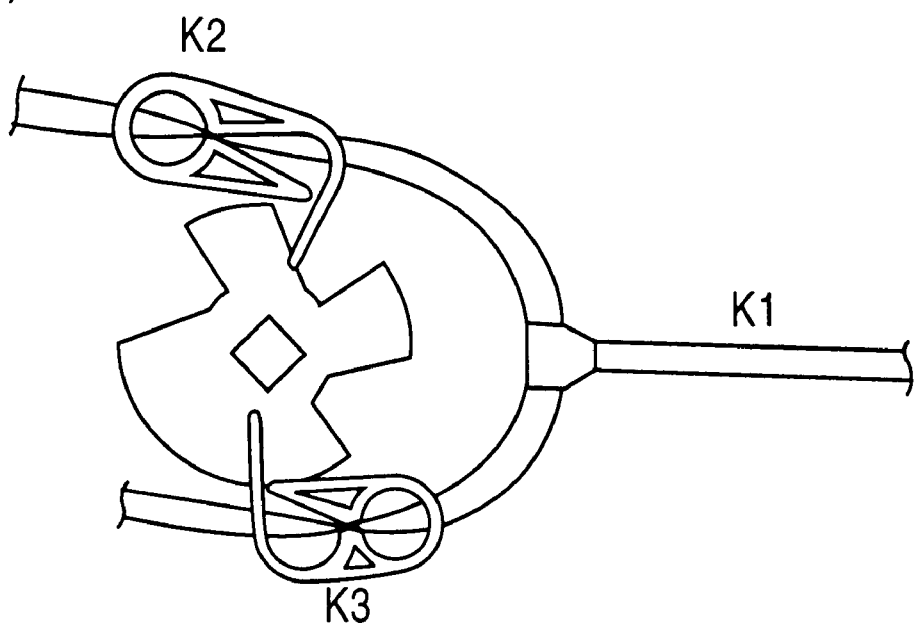

FLUID PASSAGE CHANGE-OVER APPARATUS FOR MEDICAL TREATMENT

FIELD OF THE INVENTION

The first aspect of the invention relates to a medical fluid passage switching apparatus and particularly to a fluid passage switching apparatus mounted to a Y-shaped connecting tube in a continuous ambulatory peritoneal dialysis (CAPD) system, as shown in FIG. 4.

The second aspect of the invention relates to components of the medical fluid passage switching apparatus of the first aspect and particularly to a tube employed in the apparatus.

The third aspect of the invention relates to a CAPD system employing the medical fluid passage switching apparatus of the first aspect or the medical fluid passage switching apparatus equipped with the tube of the second aspect.

PRIOR ART (1) In a conventional back-free, twin-bag system of the CAPD technology, it is necessary to operate three clamps K1, K2, and K3 in a specific order shown in Table 1, wherein said clamp K1 is mounted to a first tube 1 connected at one end to a catheter implanted in the body of a patient, said clamp K2 is mounted to a second tube 2 connected at one end to a Y-shaped joint 4 joined to the other end of the first tube 1 and at the other end to a dialysis liquid bag 5 for supplying a fresh charge of a dialysis liquid to the patient, and clamp K3 is mounted to a third tube 3 connected at one end to a drain bag 6 for collecting and discarding the charge of the dialysis liquid stored in a peritoneal cavity of the patient for a given period of time.

TABLE 1

| Initial State | K1 closed | K2 opened | K3 closed |
|---|---|---|---|
| | ↓ | ↓ | |
| Discharge | K1 opened | K2 closed | K3 opened |
| | ↓ | ↓ | |
| Flushing | K1 closed | K2 opened | K3 opened |
| | ↓ | | ↓ |
| Charge | K1 opened | K2 opened | K3 closed |
| | ↓ | ↓ | |
| End of Steps | K1 closed | K2 closed | K3 closed |

In the table, the number of steps is denoted by the arrow symbol "↓".

For completing a sequence of the steps, the patient must carry out eight actions for opening and closing the clamps. Those actions are troublesome and may be performed improperly. Also, this will discourage the application of the conventional system for a new, unskilled patient. For solving the above problems, a novel technique is developed and disclosed in PCT unexamined Japanese Publication (Tokko-Hei) 2-502882.

(2) The technique disclosed in PCT unexamined Japanese Publication (Tokko-Hei) 2-502882 has an actuator of substantially a cylindrical shape installed in substantially a tubular housing and is connected to a valve having three ports which are in turn communicated to a first, a second, and a third tube. The valve is actuated between four positions: a position for shutting off all the ports, a position for ensuring a passage is available for fluid between the first and second ports, a position for ensuring a passage is available for fluid between the second and third ports, and a position for ensuring a passage is available for fluid between the first and third ports.

However, such an arrangement requires extra means for ensuring the air-tightness and liquid-tightness in both the actuator and the housing. If the air-tightness and liquid-tightness is imperfect, bacteria existing in the air may enter the peritoneal cavity, hence causing peritonitis. According to the previous invention, the actuator and the cylindrical housing are sealed to have air-tightness and liquid-tightness with the use of O-rings which are still unsatisfactory.

DISCLOSURE OF THE INVENTION

A first object of the present invention is to provide a fluid passage switching apparatus in a medical system and particularly a fluid passage switching apparatus in a CAPD system, which at least comprises: a rotatable shaft; a cam which is rotated in relation to the rotating movement of the shaft to close and open each tube for determining the passage of fluid; and a housing so arranged to enable the holding of the cam, and having holes for running each tube therein, wherein said each tube communicating one another, and said cam consists of one member to close and open each tube for determining passages, whereby a series of fluid passage switching actions can be carried out with easier, and more particularly, to provide a fluid passage switching apparatus in a CAPD system in which a series of fluid passage switching actions can easily be carried out without producing leakage of the fluid and suffering from microbism.

A second object of the present invention is to provide a fluid passage switching apparatus having an improvement of the fitting structure of the housing in the fluid passage switching apparatus of the first object, where the housing is assembled with high accuracy to have precise dimensions but with much ease and with little chance of disassembly after initial assembly, hence giving a good enough level of safety.

A third object of the present invention is to provide a tube capable of minimizing the overall dimensions of the fluid passage switching apparatuses of the first and second objects.

A fourth object of the present invention is to provide a fluid passage switching apparatus which is improved in installing a plurality of clamps which are commonly used in each of the fluid passage in switching apparatuses of the first and second objects, are small in size, and assembled without much difficulty, for clamping the tubes, thus avoiding any assembling fault, such as the absence of a clamp.

BRIEF DESCRIPTION OF THE DRAWINGS

FIG. 6 is a diagram of a first positioning action of clamps selectively carried out in the fluid passage switching apparatus of the present invention for closing and opening, showing an initial state at (1), a discharge preparation state at (2), and a discharge state at (3);

FIG. 7 is a diagram of another positioning action of the clamps selectively carried out in the fluid passage switching apparatus of the present invention for closing and opening, showing a flushing preparation state at (4), a flushing state at (5), and a charge preparation state at (6);

FIG. 8 is a diagram of a further positioning action of the clamps selectively carried out in the fluid passage switching apparatus of the present invention for closing and opening, showing a charge state at (7), and an end-of-action state at (8);

FIG. 9 is a diagram of the first positioning action with a tube K1 controlled for closing and opening by a patient while other tubes K2 and K3 controlled with a plane cam, showing the initial state at ①, the discharge preparation state at ②, and the discharge state at ③;

FIG. 10 is a diagram of the another positioning action with the tube K1 controlled for closing and opening by a patient while the other tubes K2 and K3 are controlled with the plane cam, showing the flushing preparation state at ④, the flushing state at ⑤, and the charge preparation state at ⑥;

FIG. 11 is a diagram of the further positioning action with the tube K1 controlled for closing and opening by a patient while the other tubes K2 and K3 are controlled with the plane cam, showing the charge state at ⑦, and the end-of-action state at ⑧;

EMBODIMENTS OF THE INVENTION

Figure 1:
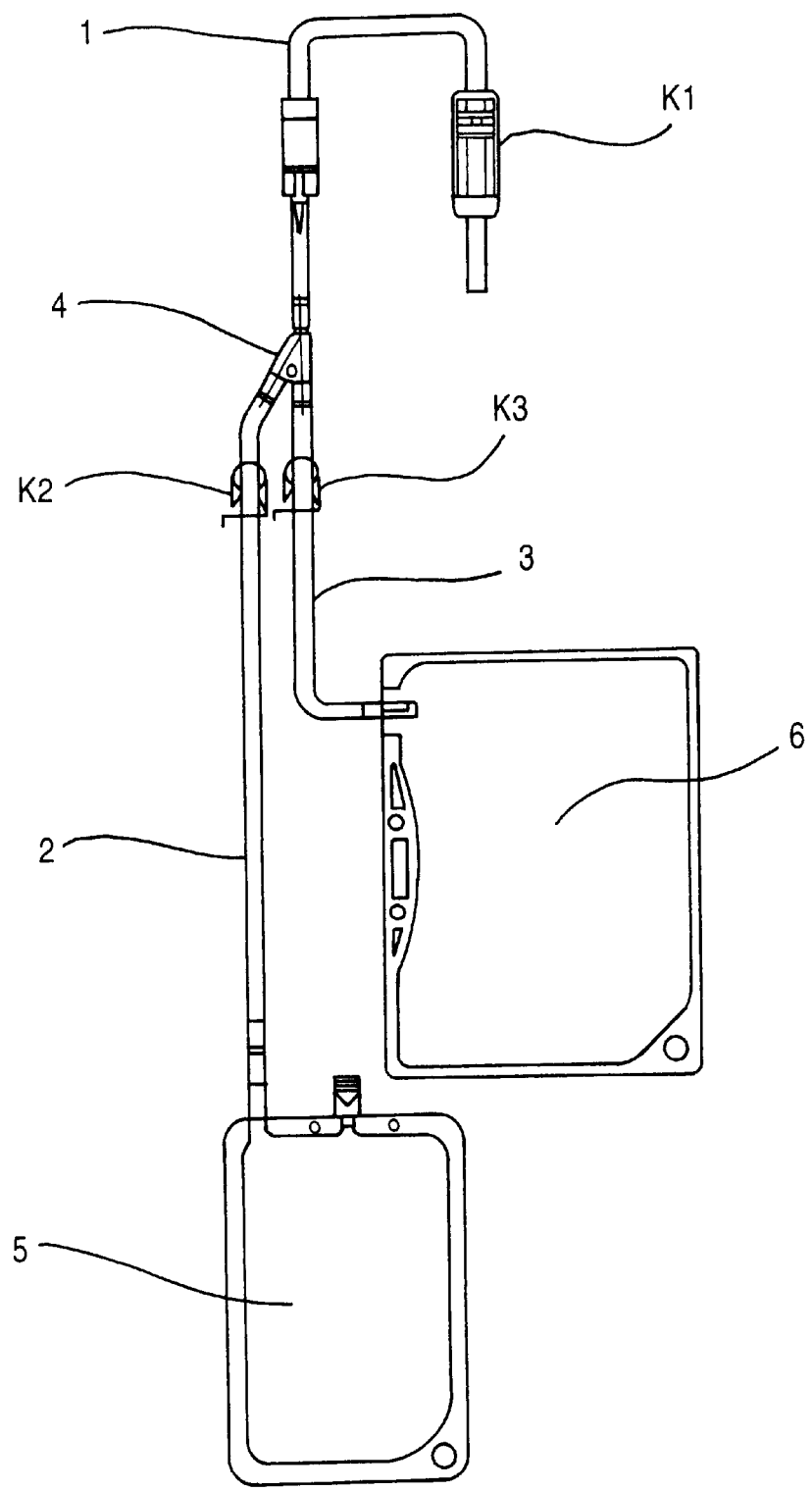
FIG. 1 is a schematic view showing a back-free, twin-bag system in a conventional CAPD method.
Figure 2:
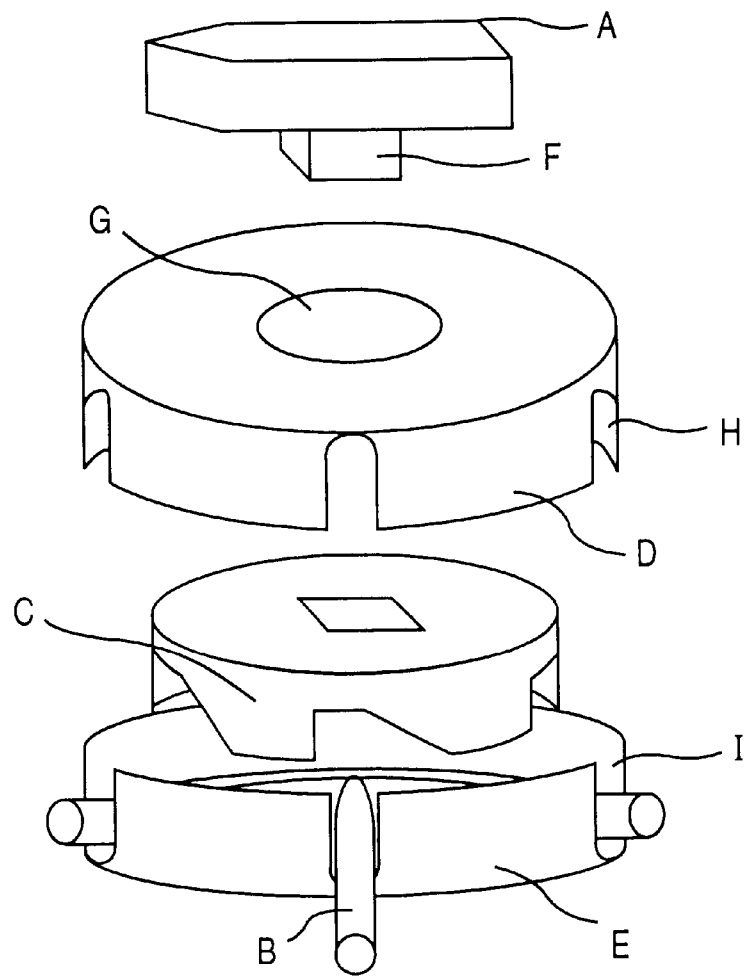
FIGS. 2 and 3 illustrate an embodiment of a fluid passage switching apparatus according to the present invention.

FIG. 2 illustrates a fluid passage switching apparatus comprising a shaft F provided with an operating handle A for pivotably holding a cam C, an upper housing shell D of a cylindrical shape having a through hole G for the shaft F and a tube accepting aperture H provided therein and arranged to fit with a lower housing shell E to form a housing for accommodating the cam, the lower housing shell E of a cylindrical shape having a tube accepting aperture I therein at a location which is opposite to the tube accepting aperture H of the upper housing shell D, and the cam C accommodated in the housing consisting of the upper housing shell D and the lower housing shell E and arranged to be rotated by the movement of the handle A to its selected positions for opening and closing a tube B.

Figure 3:
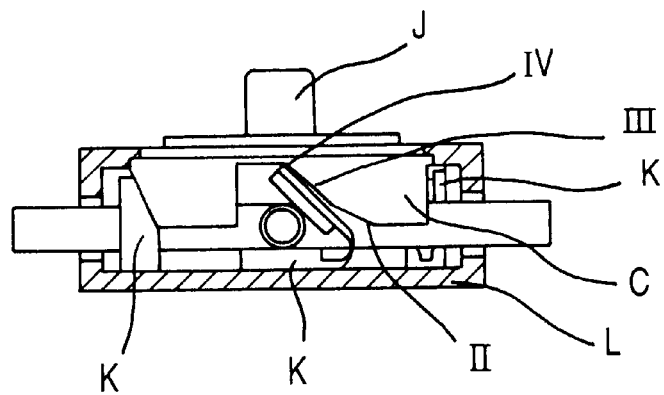

FIG. 3 shows another fluid passage switching apparatus having a cam C and an operating handle J which is formed integral with a shaft joined rotatably to the cam C held to a housing L.

Also, the present invention includes a further fluid passage switching apparatus having a member provided in a housing thereof for transmitting a force to a tube of a cam to shut the tube. The member for transmitting a force to the tube to shut the tube may be a clamp which is movable in response to a rotating movement of the cam for closing and opening the tube.

With such a fluid passage switching apparatus mounted to a Y-shaped tube joint, e.g., of a CAPD (continuous ambulatory peritoneal dialysis) system, the switching is made at particular positions listed in Table 2. The opening and closing actions of the clamp when the positions listed in Table 2 are selected in the flow passage switching apparatus of the present invention are illustrated in FIGS. 6 to 8. As shown in FIGS. 6 to 8, the tubes are open when notches of the cam come across and otherwise, they are closed. The notches are provided at intervals of 90 degrees and when moved to 45 degrees, come to their next positions.

TABLE 2

| Xposition 1 (initial state) | K1 open | K2 open | K3 open |
|---|---|---|---|
| ⊚position 2 (prepare for discharge) | K1 closed | K2 closed | K3 closed |
| *position 3 (discharge) | K1 open | K2 closed | K3 open |
| ⊚position 4 (prepare for flushing) | K1 closed | K2 closed | K3 closed |
| *position 5 (flushing) | K1 closed | K2 open | K3 open |
| ⊚position 6 (prepare for charge) | K1 closed | K2 closed | K3 closed |
| *position 7 (charge) | K1 open | K2 open | K3 closed |
| ☆position 8 (end of action) | K1 closed | K2 closed | K3 closed |

*necessary positions, Xposition required for the production, ☆preferably adopted position, ⊚preferably adopted positions in the prior art but unnecessary positions in the present invention.

The positions listed in Table 2 will now be explained in more detail.

At the initial state, the clamps K1, K2, and K3 in the fluid passage switching apparatus when released from its package remain open for preventing blocking of the tubes during sterilization.

The selection from the positions listed in Table 2 may be made by manually turning the shaft or by full or semi-automatic control of a relevant mechanism where the positions 4 to 6 are automatically controlled by time setting while the positions 1 to 3 and 6 to 8 are manually determined depending on the personal conditions of a patient such as discharge speed.

In the prior art, it is necessary to execute simultaneous actions of opening and closing the clamps K1, K2, and K3 for determining their positions listed in both Tables 1 and 2. The present invention permits the cam to systematically control a desired group of the clamps without manually operating all the clamps. For example, in the apparatus with the cam controlling all the clamps K1, K2, and K3, the position can be selected by using the handle while no action of manually opening and closing the clamps K1, K2, and K3 is needed.

Accordingly, the switching of the fluid passage can easily be carried out by a patient. Also, as the fluid passage is switched by the cam or clamps pressing down and releasing the tubes, leakage of the fluid or entry of undesired bacteria can be avoided.

The present invention is not limited to the apparatus with the cam controlling all the clamps K1, K2, and K3 and another type shown in FIGS. 9 to 11 may be implemented with a cam controlling the clamps K2 and K3 while the clamp K1 is operated by a patient.

Illustrated in FIGS. 9 to 11 are the action of the plane cam in response to the movement of a shaft for closing and opening the tubes at its positions.

Denoted by ① is the initial position, ② is the preparatory position for discharge, ③ is the discharge position, ④ is the preparatory position for flushing, ⑤ is the flushing position, ⑥ is the preparatory position for charge, ⑦ is the charge position, and ⑧ is the end of the operation.

The opening and closing states of charge and discharge tubes are listed in Table 3. In Table 3, ○ represents the opening state of the tube and X represents the closing state.

TABLE 3

| | Positions | | | | | | | |
|---|---|---|---|---|---|---|---|---|
| | ① | ② | ③ | ④ | ⑤ | ⑥ | ⑦ | ⑧ |
| Charge tube | ○ | X | X | X | ○ | X | ○ | X |
| Discharge tube | ○ | X | ○ | X | ○ | X | X | X |

In this embodiment, wherein sign N is a noxiousness bag for drainage fluid, sign M is a medicine bag for dialysis fluid and sign Pt is a patient body, and the two clamps located on the same plane are controlled with a single plane cam. It is also possible to have two or more clamps arranged in parallel and controlled with the use of a corresponding number of plane cams aligned along the same shaft 90 degrees out of phase to one another.

The components of the fluid passage switching apparatus in a medical system according to the present invention will be described in more detail.

(1) Housing

① As shown in FIG. 2, the housing comprises an upper shell D and a lower shell E. The upper shell D and the lower shell E define the space in which a cam C and clamps are accommodated. The upper shell D has a handle through hole and markings of the positions for switching the flow passage provided in and on the top side thereof. The markings include the positions 3 to 8.

Tube apertures across which the tubes to be opened and closed by the cam or the clamps extend are provided in the sides of the upper and lower shells.

② The housing is preferably shaped to a cylindrical form and sized as small as possible.

The housing may be made of metallic material such as stainless steel etc., ceramic, or heat-resistant synthetic resin such as polyacetal, polycarbonate, polypropylene, ABS resin, or polyethylene.

It is unnecessary to accommodate the cam in the housing. The housing is not limited in shape and in construction, so long as it can securely hold the shaft, the cam joined to the shaft, and the clamps, as shown in FIG. 3.

③ For ensuring the closing of the tube with the cam or a combination of the cam and the clamp while providing the operability of the cam with the handle, it is essential to assemble the upper shell D and the lower shell E to highly accurate dimensions. Particularly, ensuring the closing of the tube is most important and hence, the dimensional accuracy of the upper shell D and the lower shell E along the vertical direction (the thickness direction) is important, and towards the upward direction (a direction along which the upper shell D is separated from the lower shell E) will be even more important. The dimensional accuracy shall be affected by any faint damage produced at the joint during the assembling of the housing by joining the two shells to each other along the vertical direction.

For eliminating the above drawback, we, the inventors, joined the upper shell D and the shell E by adhesive to each other to develop a test piece and failed to have a desired level of the dimensional accuracy. A desired level of the dimensional accuracy was achieved when the two shells were assembled by thread joining, which however required a considerable length of working time. Accordingly, it was found that the thread joining was not an appropriate method in the view of practical production.

Through a series of experiments, we found that the upper shell D and the lower shell E were joined to each other for achieving the above task not by thread joining but by giving a specific fitting arrangement which is described below in more detail.

The fitting arrangement is implemented by placing the upper shell D over the lower shell E, turning it to engage its notch P with a rib Q provided on the lower shell E, and sliding and fitting a latch R of the lower shell E to a predetermined location in the notch P, as shown in FIGS. 12a and 12b. In the fitting arrangement, the engagement between the notch P of the upper shell D and the rib Q of the lower shell E determines the vertical position of the two shells D and E. When the latch R has been moved over a slope U provided on the upper shell D, its side r1 comes opposite to a facet p1 of the notch P in the engagement.

The use of the fitting arrangement permits the notch P and the rib Q for determining the vertical positioning of the housing to be free from physical damage during joining, hence achieving a desired level of dimensional accuracy in the housing. Also, the latch R of the lower shell E, the slope U and the facet p1 at the notch P of the upper shell D may be damaged due to severe friction. Such resultant damages are too small to affect the vertical dimensional accuracy of the housing.

The latch R makes the engagement between the upper and lower shells D and E easy and after the engagement, acts as a stopper which prevents the separation of the two shells from each other. Accordingly, the latch R is not limited to a particular shape while providing the above mentioned function. Preferably, the latch R has a facet r2 provided thereon for ease of the assembling the upper and lower shells. The rib Q and the latch R may be formed integral with the lower shell E or fabricated separately and then joined to the lower shell by an appropriate joining means.

The shape of the rib Q in the fitting arrangement is not of limitations while it enables engagement with the notch P for determining the vertical positioning of the upper and lower shells. Preferably for improving the strength of the apparatus, the location of the rib Q and the notch P is so determined that the edge region at the open end of the lower shell where the rib Q is provided comes into direct contact with the inner side of a circular top region of the upper shell.

Figure 12:
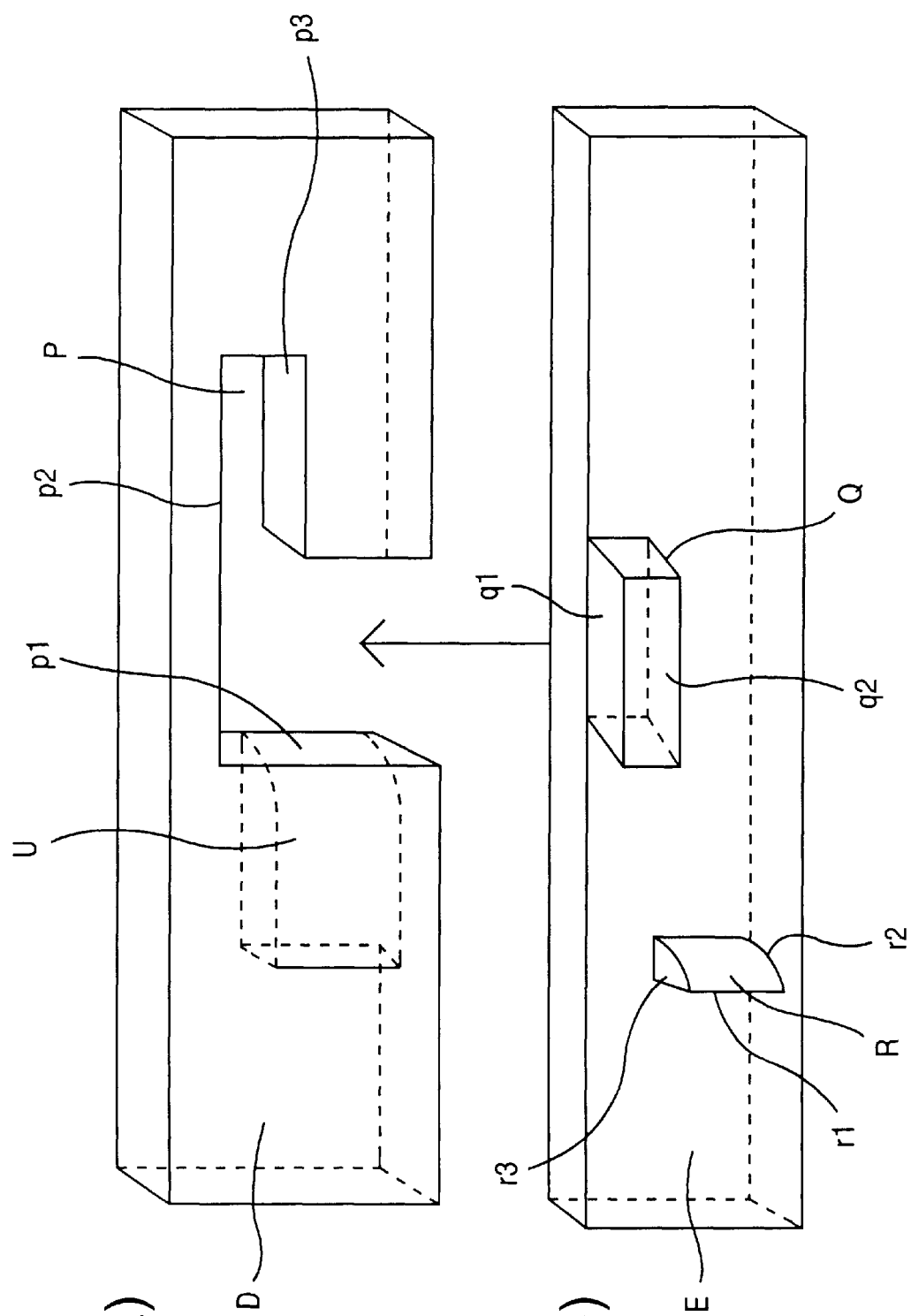
FIG. 12 is a view of shells to be assembled to a fitting structure of a housing, showing an upper shell provided with a notch at (a) and a lower shell having a rib and a latch at (b)
Figure 13:
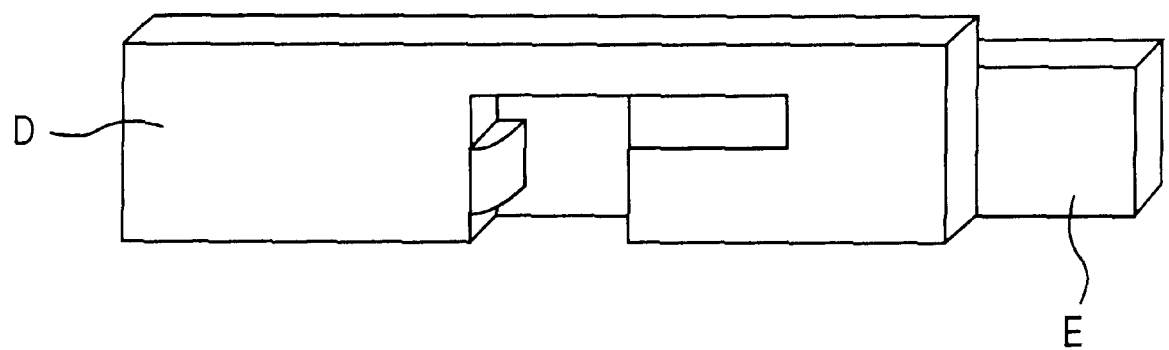
FIG. 13 is a view of the shells shown in FIG. 12 assembled together, showing the fitting structure.

The fitting arrangement is not limited to that shown in FIGS. 12 and 13, and an alternative may be used where the notch P is provided in the lower shell E while the rib Q and the latch R are provided on the upper shell D. Also, the fitting arrangement may include a means for determining the vertical positioning (particularly along the upward direction) so as to allow any two horizontally extending surfaces to directly fit each other. Although the downward positioning is determined by the facet q1 of the rib Q and the facet p2 at the notch P and the upward positioning is by the facet q2 and the facet p3 in the above example, they may be determined by the facet r3 of the latch R and the facet p2 at the notch P and by the facet q2 and the facet p3 respectively so that facet r1 of the latch R and the facet p1 at the notch P come into direct contact and are engaged with each other. Furthermore, it is possible that the dimensional accuracy along the upward direction at least is maintained by the facet q2 of the rib Q and the facet p3 at the notch P with a clearance provided between the facet q1 and the facet p2 at the notch P so that the facet r1 of the latch R and the facet p1 at the notch P directly engage each other.

Although only one of the fitting arrangements is sufficient to be provided in the housing, it is preferred to have two to five of the fitting arrangements to prevent leftward and rightward displacement of the upper shell D and the lower shell E during the turning movement of the shaft.

(2) Shaft

The apparatus allows the patient or operator to select desired one of the positions by turning the handle joined to the shaft.

(3) Cam

The cam has a construction which is rotated by the controlling action of the shaft to any desired position for opening or closing the corresponding tube directly or with the help of a clamp and may be selected from a plane cam and a solid cam.

Figure 5:
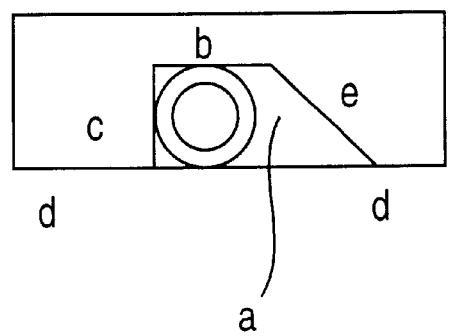
FIG. 5 illustrates a notched structure of a cam used in the fluid passage switching apparatus of the present invention.

The cam employed in the embodiment has notches provided therein as shown in FIGS. 2 and 5. The structure a of the cam shown in FIG. 5 includes a portion b for maintaining the tube at its opening state, a portion c for shifting the tube from the closing state to the opening state, a portion d (which is also denoted by signs "K" in FIG. 3) for maintaining the tube at its closing state, and a portion e for shifting the tube from the opening state to the closing state.

The distance between the portion b for maintaining the tube at its opening state and the portion d for maintaining the tube at its closing state is a length required for opening or closing the tube with or without the clamp. For example, in case that the tube is closed with the cam and its thickness is ignored, the distance is substantially identical to the diameter of the tube. When the cam is involved, its shape varies the distance which shall be higher or lower than the diameter of the tube.

The portion c for shifting the tube from its closing state to the opening state is diverted an angle of 45 to 135 degrees clockwise from the horizontal plane of the portion d and preferably, within a range from 85 to 95 degrees to prevent the reverse rotation. The angle of the portion e for shifting the tube from the opening state to the closing state is determined by the angle of the clamp. Because the strength is not required at the initial stage of closing the tube but needed at the final stage for pressing down the tube, it is preferable that the portion e consists of a steep slope III and a moderate slope II as shown in FIG. 3. The moderate slope II which transmits the pressing force of the cam continuously and lightly to the distal end IV of the clamp may preferably have a curved surface rather than a flat surface.

The cam C has a circular shape in the plan view of which the diameter is 40 to 90 percent of the diameter of the housing comprising the upper shell D and the lower shell E and more preferably 70 to 80 percent.

Figure 4:
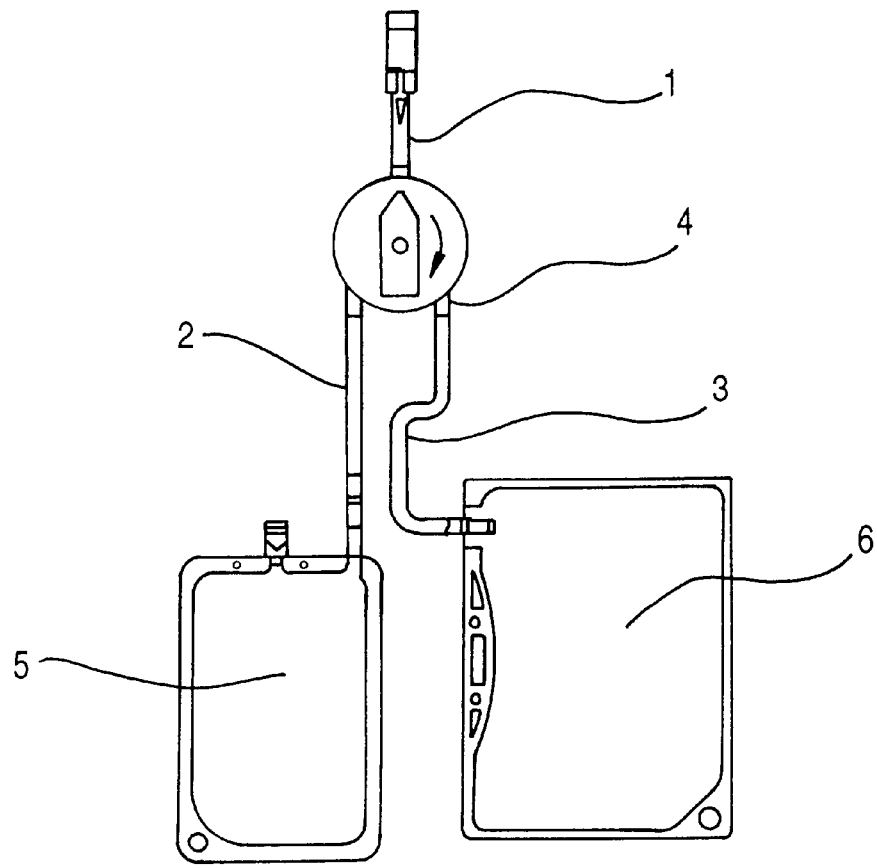
FIG. 4 is a schematic view showing a back-free, twin-bag system in a CAPD method employing the fluid passage switching apparatus of the present invention.

The number of the notches shown in FIGS. 4 and 5 is determined by the number of the positions.

When the positions are three, one notch is provided. The positions for discharge, flashing, and charge are essential as their tasks are satisfied with K2 closed, K1 closed, and K3 closed respectively. As shown in FIG. 5, one single notched structure a does the tasks. If four to eight of the positions are desired, the number of the notches is 3.

(4) Tube

① The tube commonly employed in a medical fluid passage switching apparatus (e.g. for a CAPD passage) may be of 5 mm in the inner diameter and 7 mm in the outer diameter. However, when the tube of such a size is used in the medical fluid passage switching apparatus which comprises at least a rotatable shaft, a cam arranged for turning in relation to the rotating movement of the shaft to open and close the tube which provides a fluid passage, and a housing having tube holes provided therein and arranged for accommodating the cam, the overall size of the apparatus will increase. The reason is that the diameter and the height of the cam are determined by the outer diameter of the tube, while the height of the interior space of the housing should be greater than the outer diameter of the tube. Also, as the tube is made greater in the outer diameter and the thickness, the force required on the handle has to be increased, thus disturbing the rotating operability of the handle.

② When the tube employed in a medical fluid passage switching apparatus (e.g. for a CAPD passage) is decreased in the size, the drawback that the overall dimensions of the apparatus becomes large may be eliminated. On the other hand, the reduction of the tube size, particularly the inner diameter, will reduce the flow of a fluid. For example, with a tube having 3 mm of the inner diameter instead of 5 mm in the inner diameter and 7 mm in the outer diameter, the discharge took 5% longer in duration than with the above mentioned tube. According to the present invention, the size, particularly the inner diameter, of the tube shall be determined in consideration with the duration required for the discharge caused by the reduction of diameter of the tube.

The tube having a reduced diameter may be 1 to 4 mm in the inner diameter and 2 to 5 mm in the outer diameter. It is more preferable that the inner diameter is 3.5 mm, the outer diameter is 4.5 mm, and the thickness is 0.5 mm.

Figure 14:
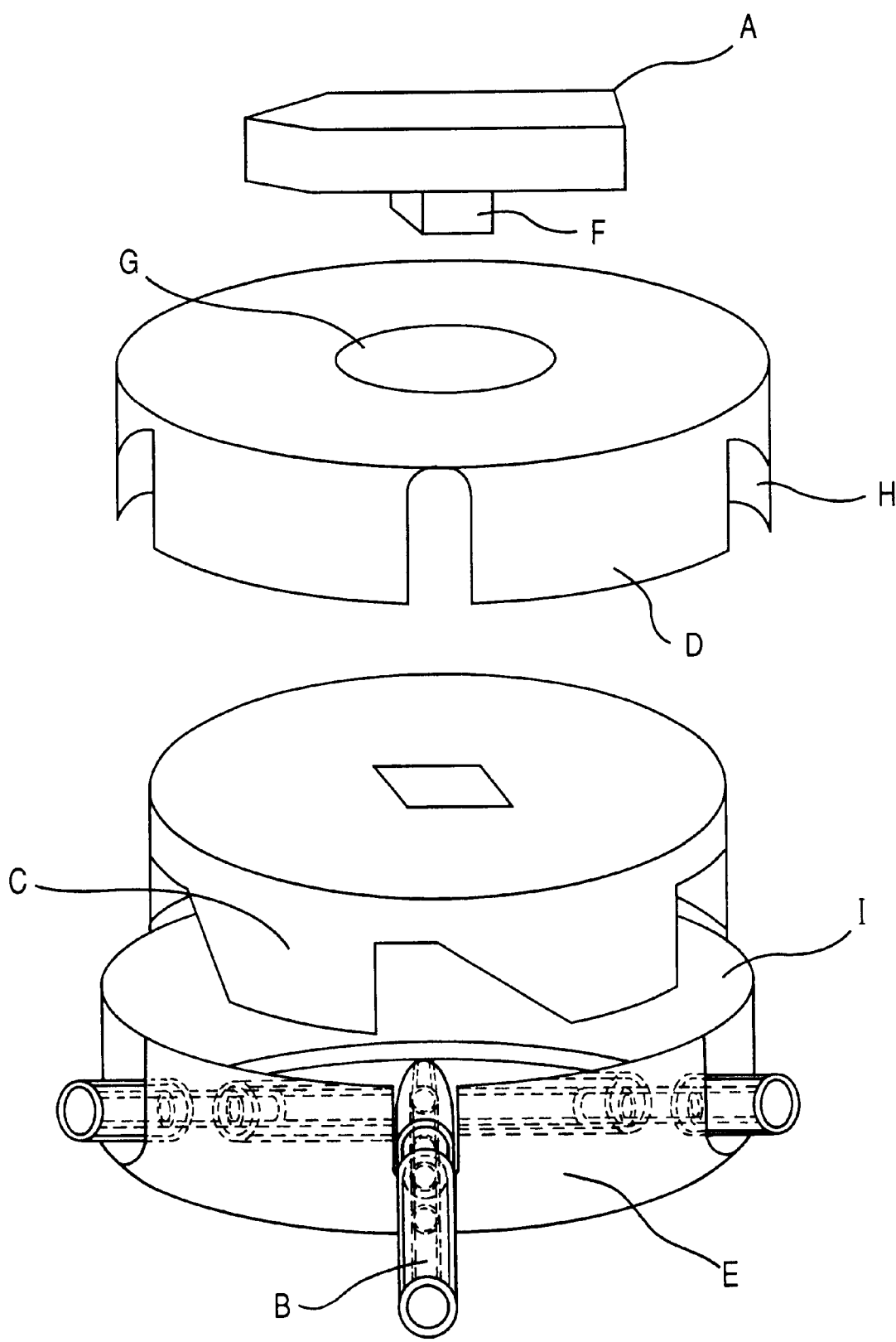
FIGS. 14 and 15 illustrate other embodiments of a fluid passage switching apparatus according to the present invention.

The diameter reduction of the tube may be implemented at each particular portion on which the clamp or a combination of the clamp and the cam presses down to open and close the tube as shown in FIG. 14. Alternatively, the entire body (of a three-directional shape) of the tube in the apparatus may be reduced in diameter. The three-directional tube may be arranged, gradually increasing its diameter from the opening/closing portion towards the open end of each directional tube.

For example, the open end of each branch of the three-directional tube is sized to 2 to 9 mm in the inner diameter and 4 to 10 mm in the outer diameter for ease of joining with conventional tubes.

The three-directional tube may be fabricated by bonding the portions of reduced diameter with other portions by adhesive or be unified by injection molding. Also, the portions other than the portions of reduced diameter may preferably be fabricated by ring-like members or a member having ring-like regions to be provided on the outer side thereof, which member(s) can sandwich from both sides the tube holes H and the through holes I provided in the housing. The ring-like members or regions permit the three-directional tube to be easily secured to the housing. The ring-like regions may be shaped by integral molding or the ring-like members may be joined to the tube by appropriate joining means.

The thickness of the tube is a critical factor for determining the strength required for ensuring the air-tightness in the tube. The smaller the thickness, the less the strength is required for ensuring the air-tightness in the tube, thus improving the rotational operability of the shaft. The thickness may be 0.1 to 1.5 mm and, more preferably, 0.3 to 0.7 mm.

Figure 15A:
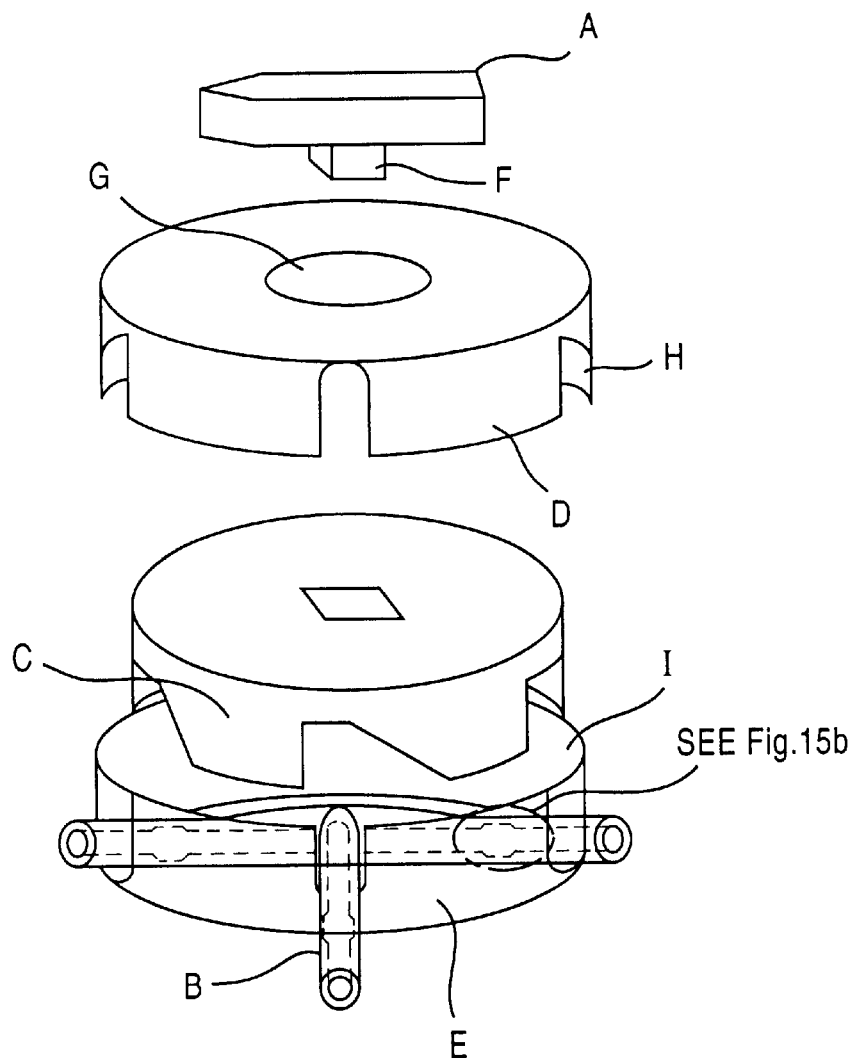
Figure 15B:
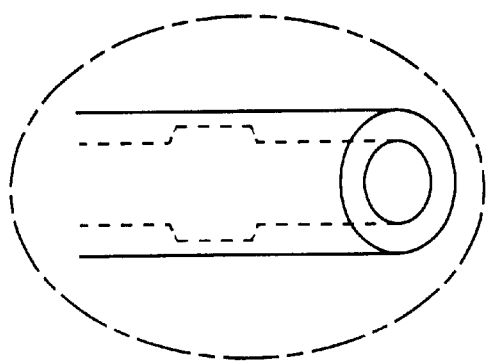

When the thickness of the tube to be closed and opened is as small as 0.3 to 0.7 mm as shown in FIG. 15, the apparatus will be of a (direct) type where the tube can directly be closed with the cam.

③ It was found through studying the reduction of the number of components and the dimensions of the medical fluid passage switching apparatus and the decrease of the height of the apparatus that while a commonly adapted tube having 5 mm of an inner diameter and 7 mm of an outer diameter suffered from damage when pressed down directly with the cam for closing and opening, the tube having a thickness of 0.3 to 0.7 mm was successfully pressed down for closing and opening by the cam without being damaged.

It is presumed that the reduction of the thickness of the tube minimizes the strength required for actuating the cam to close the tube.

In such a direct type of the apparatus, the clamp can be omitted and thus the thickness of the cam can be decreased. Accordingly, in addition to the effect of the tube having a reduced thickness of tube wall and reduced inner diameter, the medical fluid passage switching apparatus can be minimized in the number of its components, reduced in the height, and designed to have a compact structure. Also, as the direct type of the apparatus is shortened along the radial direction as well as in the thickness direction, its overall dimensions can further be reduced.

(5) Clamp

The clamp is preferably fabricated comprising a pair of projections for closing and opening the tube in relation with the movement of the cam and an arcuate member joining the two projections. When the clamp has moved from the portion d via the portion c to the portion b at the notch of the cam, the tube is released. Since its arcuate member has a self-returning-back function, the clamp will hardly prevent the recovering action by the resiliency of tube, thus ensuring quick opening of the tube. However, the clamp in the present invention is not limited to a structure described above and other structures will be used, including one having the two projections joined by a hinge to each other at corresponding recessed regions and another having a pair of sheet-like members slidably supported on a bridge member.

In case that the medical fluid passage switching apparatus of the present invention includes a plurality of the clamps, the clamps may be provided in a single unit or each clamp may be formed integral with another component. For example, the upper parts (which are closer to the cam than to the tube) of the clamps are formed as a single unit, and the lower parts (which are closer to the tube than to the cam) of the clamps are formed as a single unit. This will eliminate the difficulty of the clamps being installed during the assembling of the medical fluid passage switching apparatus or avoid such an assembling fault as the absence of a clamp.

The lower parts of the clamps may be formed integral with the inner wall of the lower shell E of the housing. Since the clamps are formed as units, the number of components in the apparatus will be minimized and the overall height of the apparatus will be reduced.

When the medical fluid passage switching apparatus of the present invention is of the direct type, the lower parts (which are closer to the tube than to the cam) of the clamps may also be formed as a single unit. Similar to the above case, the upper parts may be formed integral with the inner wall of the lower shell E of the housing.

The cam in said direct type apparatus may preferably be reduced in the thickness of the portion of the wall to close the tube in comparison with the cam used in the apparatus type using the clamps. The configuration of the portion having the role to close the tube in the cam is preferably formed having a curved shape. Furthermore, it is favorable to form projections in lower parts of cam to fit into the recess formed in lower parts of clamps.

With the use of the medical fluid passage switching apparatus and the tube according to the present invention, the fluid passage switching action by a patient will be carried out with ease. Also, the passage is switched by the cam or the clamps pressing down and releasing the tubes and hence leakage of the fluid or entry of undesired bacteria will be avoided.

The medical fluid passage switching apparatus of the present invention is effectively used as a Y-shaped tube joint form of a fluid passage switching apparatus in a CAPD (continuous ambulatory peritoneal dialysis) system. Also, the same apparatus may replace a conventional fluid passage switching apparatus in a fluid passage system which is commonly employed in the form of a three-directional valve.

When the medical fluid passage switching apparatus of the present invention is used in such a known system, various problems with the three-directional valve including leakage of a fluid and entry of unwanted bacteria will be eliminated. Such a known system may be an infusion system. Also, the apparatus is applicable in a system for doping a mixture of different medical liquids provided by single fluid preparation (simultaneous mixing) (e.g. a mixture of glucose and a liquid containing amino acid and electrolysis for nutrition infusion and a mixture of a carbonic acid contained liquid and a glucose contained liquid for bicarbonate contained peritoneal dialysis), a blood circuit, a transfusion system, or a blood components separating system.

What is claimed is:

1. A medical fluid passage switching apparatus comprising:
   a rotatable shaft;
   a plurality of tubes each being driven by said rotatable shaft for determining a passage of fluid;
   a cam being rotated in relation to the rotating movement of said shaft to close or open each of said tubes; and
   a housing for holding said cam and having holes for passing said tubes therethrough, wherein said tubes are communicating one another, and said cam is provided with a valve member to close or open said tubes for determining said passages.

2. A medical fluid passage switching apparatus according to claim 1, wherein said housing has an axis hole which makes to penetrate the rotatable shaft and said cam is accommodated in said housing.

3. A medical fluid passage switching apparatus according to claim 1, further comprising members which transmit a force of said cam to their respective tubes to close down the tubes.

4. A medical fluid passage switching apparatus according to claim 3, wherein said members for transmitting the force of the cam to close down the tubes are clamps.

5. A medical fluid passage switching apparatus according to claim 1, wherein said cam has a notched structure (a) comprising a portion (b) for maintaining the opening state of the tube, a portion (c) for shifting the tube from the closing state to the opening state, a portion (d) for maintaining the closing state of the tube, and a portion (e) for shifting the tube from the opening state to the closing state.

6. A medical fluid passage switching apparatus according to claim 5, wherein the portion (e) for shifting the tube from the opening state to the closing state is tilted having a sharp slope at the front and a moderate slope at the rear.

7. A medical fluid passage switching apparatus according to claim 6, wherein the moderate slope is a curved surface.

8. A medical fluid passage switching apparatus according to claim 4 or 5, wherein the clamps are joined together as a unit or formed integral with another component.

9. A medical fluid passage switching apparatus according to claim 8, wherein upper parts and/or lower parts of the clamps are joined together as a unit.

10. A medical fluid passage switching apparatus according to claim 9, wherein the lower parts of the clamps are formed integral with a lower shell of the housing.

11. A medical fluid passage switching apparatus according to claim 1, wherein at least one of said tubes is decreased in the diameter at a region where the cam or a combination of the cam and the clamp is engaged with for closing or opening as compared with at the remaining regions.

12. A medical fluid passage switching apparatus according to claim 1, wherein at least one of said tubes is thinned in the wall at a region where the cam or a combination of the cam and the clamp is engaged with for closing or opening as compared with at the remaining regions.

13. A medical fluid passage switching apparatus according to claim 1, wherein at least one of said tubes is decreased in the diameter and thinned in the wall at a region where the cam or a combination of the cam and the clamp is engaged with for closing or opening as compared with at the remaining regions.

14. A medical fluid passage switching apparatus according to claim 11, 12, or 13, wherein its shape of said tubes is a three-directional branched configuration.

15. A CAPD (continuous ambulatory peritoneal dialysis) system including the medical fluid passage switching apparatus defined in any of claim 2 or 5.

* * * * *